United States Patent [19]

Dockner et al.

[11] 4,340,745
[45] Jul. 20, 1982

[54] PREPARATION OF 2-IMIDAZOLINES

[75] Inventors: Toni Dockner, Meckenheim; Uwe Kempe, Limburgerhof; Herbert Krug, Ludwigshafen; Peter Magnussen, Bad Durkheim; Werner Praetorius, Ludwigshafen, all of Fed. Rep. of Germany

[73] Assignee: BASF Aktiengesellschaft, Ludwigshafen, Fed. Rep. of Germany

[21] Appl. No.: 242,011

[22] Filed: Mar. 9, 1981

[30] Foreign Application Priority Data

Mar. 13, 1980 [DE] Fed. Rep. of Germany ....... 3009633

[51] Int. Cl.³ .......................................... C07D 231/06
[52] U.S. Cl. .................................... 548/347; 548/355
[58] Field of Search .............................. 548/347, 355

[56] References Cited

U.S. PATENT DOCUMENTS 3,388,132  6/1968  Kroeper et al. .................... 548/335
3,629,278  12/1971  Bachman ............................ 548/347

FOREIGN PATENT DOCUMENTS 1189998   4/1965  Fed. Rep. of Germany.
1231242  12/1966  Fed. Rep. of Germany.
1231249  12/1966  Fed. Rep. of Germany.
1922802  11/1970  Fed. Rep. of Germany.
2729017   1/1979  Fed. Rep. of Germany.

OTHER PUBLICATIONS

Journal of the American Chemical Society 95 (1973) 4,447–4,448.
Ullmanns Encyklopädie der technischen Chemie, vol. 13, pp. 331–338.

Primary Examiner—Henry R. Jiles
Assistant Examiner—Bernard Dentz
Attorney, Agent, or Firm—John H. Shurtleff

[57] ABSTRACT

2-Imidazolines are prepared by reacting N,N'-diformyl-1,2-diamines in the gas phase at 200°–350° C., in the presence of certain amounts of an inert gas, over zinc oxide of a particular structure or over a mixture of this zinc oxide and aluminum oxide, as the catalyst.

The 2-imidazolines obtainable by the process according to the invention are valuable starting materials for the preparation of dyes, crop protection agents and drugs.

15 Claims, No Drawings

PREPARATION OF 2-IMIDAZOLINES

The present invention relates to a novel process for the preparation of 2-imidazolines by reacting N,N'-diformyl-1,2-diamines in the gas phase at 200°-350° C., in the presence of certain amounts of an inert gas, over zinc oxide of a particular structure or over a mixture of this zinc oxide and aluminum oxide, as the catalyst.

The reaction of formaldehyde with diaminoalkanes in the presence of sulfur gives 2-imidazolines, but hydrogen sulfide is also formed in stoichiometric amounts. German Laid-Open Application DOS 1,189,998 describes the synthesis of 2-imidazolines by reacting diaminoalkanes with hydrocyanic acid. This process has the disadvantages that the yield is in some cases unsatisfactory, and that hydrocyanic acid has to be handled on an industrial scale.

The reaction of diaminoalkanes with tert.-butyl isonitrile, in the presence of silver cyanide, to give 4,5-dihydroimidazole, is also known (J. Amer. Chem. Soc., 95 (1973), 4,447-4,448). The yields are satisfactory, but tert.-butyl isonitrile creates an odor nuisance and, on the grounds of safety of operation and environmental protection alone, makes the process unsuitable for operation on a larger scale.

German Laid-Open Application DOS 1,922,802 discloses that N,N'-diformyl-1,2-diaminoalkanes may be converted to 2-imidazolines at from 400° to 600° C. over activated silica or silicates in a fixed bed reactor, advantageously under pressures of from 1 to 100 mm Hg. However, disadvantages of this process are the low pressures, and the ease with which 2-imidazolines decompose, as described in U.S. Pat. No. 3,629,278. An essential feature of the process is a reaction pressure of less than 200 mm Hg; in the Example given, a pressure of from 0.25 to 100 mm Hg is employed. Such a low pressure would be a disadvantage in the continuous preparation of 2-imidazolines on an industrial scale. DE-OS 1,922,802 states that 2-imidazolines cannot be prepared from N,N'-diformylalkylenediamines by other methods.

We have found that 2-imidazolines of the formula

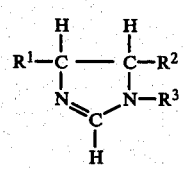

where $R^1$, $R^2$ and $R^3$ may be identical or different and each is an aliphatic, araliphatic or aromatic radical or is hydrogen, may be obtained in an advantageous manner by reacting an N,N'-diformylalkylenediamine over a metal oxide catalyst, if an N,N'-diformyl-1,2-diamine of the formula

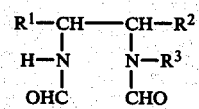

where $R^1$, $R^2$ and $R^3$ have the above meanings, is reacted in the gas phase, at from 200° to 350° C., in the presence of from 5 to 40 moles of an inert gas per mole of starting material II, over zinc oxide having a pore volume of from 0.05 to 1 milliliter per gram and a specific surface area of from 1 to 500 square meters per gram, or over a mixture of this zinc oxide and aluminum oxide, as the catalyst.

If N,N'-diformyl-1,2-diaminopropane is used, the reaction can be represented by the following equation:

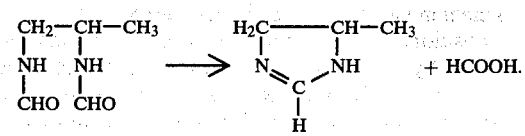

Compared to the conventional processes, the process according to the invention gives 2-imidazolines more simply and more economically and in some cases in better yield and greater purity. The use of sulfur compounds and hydrocyanic acid compounds as reactants is avoided, and nevertheless surprisingly high yields are achieved. The reaction does not have to be carried out under reduced pressure. It is advantageous that the process takes place in the gas phase; thus 2-imidazolines, which are unstable in the liquid phase, can be reacted further without prior isolation. For example, the dehydrogenation of the relatively unstable 2-imidazoline to give the stable imidazole can easily be carried out in a second reaction stage, in the gas phase. All these advantageous results specifically also permit industrial continuous operation, with the catalyst exhibiting a long life, and are surprising in view of the prior art. In the light of U.S. Pat. No. 3,629,278 and of German Laid-Open Application DOS 1,922,802 it would have been expected that the different catalysts used would have produced no reaction or would at least have caused a great diminution in yield. In particular it had to be assumed, in the light of German Pat. No. 1,231,249 and of German Laid-Open Application DOS 2,729,017, that the end products obtained would essentially be imidazoles. A further surprising result, compared to the process described in German Pat. No. 1,231,249 (Example 4), is that at temperatures above 250° C., and carrying out the reaction over zinc oxide of the structure prescribed according to the invention, 2-imidazoline is formed in high yield in place of imidazole. On the other hand it was also not to be expected, in view of German Laid-Open Application DOS 2,729,017, Example 2, that the use of the starting material II according to the invention in place of ethylenediamine and formic acid would give imidazoline instead of imidazole in high yield even at above 300° C.

Preferred starting materials II and accordingly preferred end products I are those where $R^1$, $R^2$ and $R^3$ are identical or different and each is alkyl of 1 to 18 carbon atoms, especially of 1 to 8 carbon atoms, alkenyl with a plurality of double bonds or more especially with one double bond and of 2 to 18, preferably 3 to 18, especially 4 to 8, carbon atoms, aralkyl or alkylaryl of 7 to 12 carbon atoms or phenyl or hydrogen. The above radicals may additionally be substituted by groups which are inert under the reaction conditions, for example alkyl or alkoxy each of 1 to 4 carbon atoms.

Examples of starting materials II are the N,N'-diformyl compounds of ethylenediamine, 1,2-propylenediamine, 1,2-butylenediamine, 1,2-pentylenediamine, 1,2-n-hexylenediamine, 1,2-n-heptylenediamine, 1,2-n-octylenediamine, 1,2-n-nonylenediamine, 1,2-n-decylenediamine, 1,2-n-octadecylenediamine, 2,3-butylenediamine, 2,3-pentylenediamine, 2,3-hexylenediamine, 2,3-heptylenediamine, 2,3-octylenediamine, 2,3-nonylenediamine, 2,3-decylenediamine, 3,4-hexylenediamine, 3,4-heptylenediamine, 3,4-octylenediamine, 3,4-nonylenediamine, 3,4-decylenediamine, 4,5-octylenediamine, 4,5-nonylenediamine, 4,5-decylenediamine and 5,6-decylenediamine, ethylenediamines monosubstituted in the 1-position, or substituted in both the 1- and the 2-position, by benzyl and/or phenyl, and ethylenediamines substituted by the above alkyl groups in the 1-position and by benzyl or phenyl in the 2-position; and the N-methyl-, N-ethyl-, N-propyl-, N-isopropyl-, N-butyl-, N-isobutyl-, N-sec.-butyl-, N-tert.-butyl-, N-benzyl- and N-phenyl derivatives of the above N,N'-diformyl-1,2-diamines.

The reaction is carried out at from 200° to 350° C., advantageously from 250° to 350° C., preferably from 260° to 340° C., especially from 270° to 330° C., under atmospheric or superatmospheric pressure, as a rule under not less than 1 bar, advantageously under from 1 to 10, preferably from 1 to 3, bar, batchwise or, advantageously, continuously. As a rule, the reaction mixture also serves as the solution medium; where appropriate, organic solvents which are inert under the reaction conditions and which advantageously do not form an azeotrope with water may also be used, for example aliphatic hydrocarbons, eg. petroleum ether or naphtha. Amongst the organic solvents, those of boiling point above 120° C., advantageously above 140° C., for example appropriate gasoline fractions of boiling range 120°–160° C., are preferred.

The catalyst used is zinc oxide alone or a mixture of zinc oxide and aluminum oxide, advantageously in a ratio of from 1 to 50, preferably from 8 to 10, gram atoms of zinc per gram atom of aluminum. Advantageously from 0.1 to 1, preferably from 0.2 to 0.4, gram atom of zinc is employed per mole of starting material II. Suitable aluminum oxides are, for example, $\alpha$- and $\gamma$-alumina. It is also possible to use zinc compounds which form zinc oxide under the reaction conditions, for example aluminum oxide impregnated with zinc chloride or with zinc sulfate. Instead of aluminum oxide, materials, or mixtures of materials, which contain this oxide may also be used, for example aluminum silicate, magnesium aluminum silicate hydrate, dimagnesium aluminum silicate hydrate, sodium aluminum silicate, calcium aluminum silicate, fuller's earth, clays, bleaching earths (eg. bentonite), bauxite, pumice, andalusite, kaolin, allophanes, zeolites, mullite, corundum, hydrargillite and boehmite.

The catalyst may be unsupported, or may be on a carrier, advantageously in an amount of from 1 to 18 percent by weight of catalyst, based on the carrier. Equally, the above aluminum compounds may simultaneously serve as a catalyst component, by virtue of the $Al_2O_3$ which they contain, and as a carrier for the zinc oxide. Advantageous carriers are silica and silica compounds, such as silicates, eg. montmorillonite, Florida earth, quartz and asbestos; precipitated silica, silica gel and kieselguhr; titanium dioxide, zirconium dioxide, tin dioxide and active charcoal; alkaline earth metal sulfates and alkaline earth metal phosphates, eg. the calcium and barium salts; and appropriate mixtures of the above carriers. The supported catalysts are prepared by conventional methods, for example by applying the zinc compound, with or without the aluminum compound, to a carrier, drying and calcining, for example at from 400° to 1,200° C. in a reducing, oxidizing or inert atmosphere. It is also possible to impregnate the carrier, in its desired geometrical form, with a solution of the zinc compound alone or of the zinc compound and the aluminum compound, for example an aqueous solution containing zinc sulfate with or without aluminum sulfate, and then to dry the impregnated material. Equally, it is possible to knead the carrier with the zinc compound, with or without the aluminum compound, and with water and to mold the kneaded material, dry it and calcine it at from 400° to 1,200° C.

The particle size of the catalyst is preferably from 0.05 to 7, especially from 2 to 4, millimeters. It can be of any desired shape, for example in the shape of pills, cylinders, extrudates, beads or granules. The catalyst has a pore volume of from 0.05 to 1, preferably from 0.1 to 0.8, milliliter per gram and a specific surface area of from 1 to 500, preferably from 30 to 150, square meters per gram. The catalyst preferably has a bulk density of from 0.4 to 2.1 grams per milliliter. For the purposes of the present invention, the specific total surface area is the total inner and outer surface area of 1 gram of catalyst. This specific total surface area can be determined by the conventional methods, for example the BET method (Ullmanns Encyklopädie der technischen Chemie, Volume 9, page 266). In general, the pore radius of the catalyst is from 1.5 to 10, advantageously from 3 to 8, nanometers. Catalyst-coated tubes or catalysts supported on mesh-like carriers may also be used.

Preferably, the catalyst is employed in chip or bead form in the fluidized bed, the catalyst particles advantageously having sizes of from 0.005 to 3 mm, especially from 0.1 to 1 mm, preferably from 0.2 to 0.4 mm. The height of the fluidized catalyst bed is advantageously from 30 to 3,000 millimeters, or is so chosen as to give a residence time of the starting material II in the catalyst bed of from 0.01 to 20, preferably from 1 to 10, seconds. Regarding the preparation of the catalysts, reference may be made to Houben-Weyl, Methoden der Organischen Chemie, Volume 4/2, pages 142 et seq. and Ullmanns Encyklopädie technischen Chemie, Volume 9, page 271 et seq.

Where appropriate, other oxides, for example iron-III oxide, may be used as auxiliary catalysts together with the zinc oxide; a suitable amount is from 0.2 to 2, especially from 0.8 to 1.2, moles of Fe-(III) oxide per mole of zinc oxide. An advantageous combination is zinc oxide and iron-III oxide on a silicon dioxide carrier, for example on silica or silica gel, advantageously using from 12 to 20 percent by weight of $Fe_2O_3$, based on $SiO_2$, and from 150 to 250 percent by weight of $Fe_2O_3$, based on ZnO.

As gases which are inert under the reaction conditions, it is advantageous to use noble gases, eg. xenon, argon, neon and helium, alkanes, eg. methane, ethane, propane, 2,2-dimethylpropane, butane, pentane and isobutane, or, preferably, nitrogen, carbon monoxide and/or carbon dioxide, or mixtures of the above. The exit gas from the reaction according to the invention can advantageously be recycled, this recycle gas serving as the inert gas. The recycle gas advantageously contains from 0 to 80 percent by weight of nitrogen, from 5 to 20 percent by weight of $CO_2$, from 5 to 90 percent by weight of carbon monoxide, from 0.1 to 3 percent by weight of hydrogen, from 2.5 to 10 percent by weight of steam, from 0.01 to 2 percent by weight of alkane formed from the starting material II, from 0.01 to 2 percent by weight of alkene formed from the starting material II, and from 0.2 to 2.5 percent by weight of ammonia. Preferably, from 7 to 38, especially from 9 to 36, moles of inert gas are used per mole of starting material II.

The reaction may be carried out as follows: the vaporous starting material II, mixed with inert gas, is passed, at the reaction temperature, over the catalyst or supported catalyst in a tubular reactor or fluidized bed reactor. A residence time of from 1 to 40, especially from 1 to 20, seconds in the reaction space is advantageous. The end product is isolated in a conventional manner, for example by fractional distillation, from the reaction mixture leaving the reactor. However, it is also possible to take samples of the reaction mixture, ascertain the conversion by analytical, for example gas-chromatographic, determination of the ratio of end product I to starting material II in the reaction mixture, and directly convert the reaction mixture further, without isolating the end product, for example convert it to the corresponding imidazoles.

In a preferred embodiment of the process, the starting materials are reacted in a fluidized bed at the reaction temperature. The catalyst or supported catalyst can advantageously be maintained in a fluidized bed by employing an inert gas, or a mixture of starting material II and inert gas, as the fluidizing gas under superatmospheric pressure. It is also possible to maintain the starting material in the liquid state in a heated stock vessel and meter it from there into a vaporizer, upstream from the fluidized bed reactor, whilst at the same time advantageously passing a stream of inert gas, advantageously at the rate of from 5,000 to 50,000 parts by volume per hour, through the vaporizer. The vaporized starting material is thus passed with the stream of inert gas through the catalyst bed. The process according to the invention can be carried out in a simple or compartmented, open or closed, fluidized bed system, with or without fly dust recycling. For details of reactors, operation, process variants and reaction conditions employed in fluidized bed processes, reference may be made to Ullmanns Encyklopädie der technischen Chemie, Volume 1, pages 916 et seq. The reaction mixture is worked up in the manner described above.

The 2-imidazolines I obtainable by the process according to the invention are valuable starting materials for the preparation of dyes, crop protection agents and drugs.

2-Imidazolines I are also employed as catalysts for polymerization reactions and aldol condensations. When dehydrogenated over alumina/zinc oxide catalysts, they give the corresponding imidazoles. Regarding the use of imidazoles, reference may be made to the above publications and to Ullmanns Encyklopädie der technischen Chemie, Volume 13, pages 331 and 338.

In the Examples which follow, parts are by weight, and bear the same relation to parts by volume as that of the kilogram to the liter.

EXAMPLE 1

56 parts per hour of N,N'-diformyl-1,2-diaminoethane are metered from a stock vessel into a horizontal quartz vaporizer heated to 300° C. and the vapor, together with 400 parts by volume of nitrogen per hour, is passed through a fluidized bed reactor heated to 300° C. This reactor is a vertical electrically heated quartz tube, located on the vaporizer, and terminating at the bottom in a fused-in quartz frit. The quartz tube is half filled with 220 parts of a catalyst (bulk density 1.3 grams per milliliter) consisting of 10 percent by weight of ZnO and 90 percent by weight of γ-alumina (pore volume 921 milliliters per gram; specific surface area 83.3 square meters per gram; pore radius 8 nanometers). The residence time in the fluidized catalyst zone is 1.0 second. The height of the fluidized catalyst zone is 150 mm. The vapors leaving the reactor are condensed and subjected to fractional distillation. Per hour, 31.4 parts (92.9% of theory) of 2-imidazoline, of boiling point 105° C./32 mbar, are obtained. The conversion is virtually quantitative. The yield remains constant even after 1,500 hours' operation.

EXAMPLE 2

The procedure followed is as described in Example 1, except that 220 parts of zinc oxide (structure similar to that in Example 1) are employed. Per hour, 27 parts (79.8% of theory) of 2-imidazoline, of boiling point 105° C./32 mbar, are obtained. The conversion is virtually quantitative. The yield remains constant even after 1,500 hours' operation.

EXAMPLE 3

The procedure followed is as described in Example 1, except that 220 parts of a catalyst (bulk density 0.65 gram per milliliter) consisting of zinc oxide (structure similar to Example 1) and aluminum oxide in a weight ratio of 1:4 are employed. Per hour, 29.8 parts (88.1% of theory) of 2-imidazoline, of boiling point 105° C./32 mbar, are obtained. The conversion is virtually quantitative. The yield remains constant even after 1,500 hours' operation.

EXAMPLE 4

The procedure followed is as described in Example 1, except that 220 parts of a catalyst (bulk density 0.9 gram per milliliter) consisting of zinc oxide (structure similar to Example 1) and aluminum oxide in a weight ratio of 1:1 are employed. Per hour, 29.4 parts (87% of theory) of 2-imidazoline, of boiling point 105° C./32 mbar, are obtained. The conversion is virtually quantitative. The yield remains constant even after 1,500 hours' operation.

EXAMPLE 5

The procedure followed is as described in Example 1, except that 220 parts of catalyst (bulk density 0.8 gram per milliliter) containing 6.6 percent by weight of ZnO and 13 percent by weight of $Fe_2O_3$ on silicon dioxide (pore volume 0.11 milliliter per gram; specific surface area 45 square meters per gram; pore radius 74 nanometers) are employed. 49.9 parts per hour of N,N'-diformyldiaminoethane are introduced into the catalyst zone. 27.5 parts per hour (91.3% of theory) of 2-imidazoline, of boiling point 105° C./32 mbar, are obtained. The conversion is virtually quantitative. The yield remains constant even after 1,100 hours' operation.

EXAMPLE 6

The procedure followed is as described in Example 1, except that 200 parts of a catalyst (bulk density 0.73 gram per milliliter) consisting of zinc oxide (structure similar to Example 1) and aluminum oxide in a weight ratio of 3:7 are employed. 70 parts per hour of N,N'-diformyl-1,2-diaminopropane are introduced into the catalyst zone at 290° C. 40.3 parts per hour (89% of theory) of 4(5)-methyl-2-imidazoline, of boiling point 94° C./20 mbar, are obtained. The conversion is virtually quantitative. The yield remains constant even after 1,500 hours's operation.

EXAMPLE 7

The procedure followed is as described in Example 1, except that 220 parts of a catalyst (bulk density 1.3 grams per milliliter) consisting of zinc oxide (structure similar to Example 1) and aluminum oxide in a weight ratio of 9:1 are employed. 70 parts per hour of N,N'-diformyl-1,2-diaminopropane are reacted at 320° C. 42 parts per hour (92.9% of theory) of 4(5)-methyl-2-imidazoline, of boiling point 94° C./20 mbar, are obtained. The conversion is virtually quantitative. The yield remains constant even after 1,500 hours' operation.

EXAMPLE 8

The procedure followed is as described in Example 1, except that 220 parts of a catalyst (bulk density 1.3 grams per milliliter) consisting of zinc oxide (structure similar to Example 1) and aluminum oxide in a weight ratio of 9:1 are employed. 75 parts per hour of N,N'-diformyl-1,2-diaminobutane are reacted at 290° C. 56.5 parts per hour (97% of theory) of 4(5)-ethyl-2-imidazoline, of boiling point 114° C./25 mbar, are obtained. The conversion is virtually quantitative. The yield remains constant even after 1,500 hours' operation.

EXAMPLE 9

80 parts per hour of solid N,N'-diformylethylenediamine from a stock vessel and 680 parts per hour of recycle gas are passed through a fluidized bed reactor heated to 320° C. The reactor is filled with 1,500 parts of catalyst (bulk density 1.3 grams per milliliter) consisting of zinc oxide (structure similar to that in Example 1) and aluminum oxide in a weight ratio of 9:1. Proceeding similarly to Example 1, 42.5 parts per hour (88% of theory) of 2-imidazoline, of boiling point 105° C./32 mbar are obtained. The exit gas is freed from volatile constituents in a wash column and is then dried by cooling and employed as recycle gas (fluidizing gas and dilution gas). The recycle gas contains 90 percent by weight of CO, 8 percent by weight of $CO_2$ and 2 percent by weight of hydrocarbons. 17 parts per hour of the recycle gas are taken off. The conversion is virtually quantitative. The yield remains constant even after 1,500 hours' operation.

We claim:

1. In a process for the preparation of a 2-imidazoline of the formula

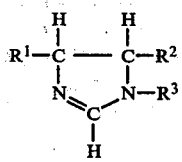

where $R^1$, $R^2$ and $R^3$ may be identical or different and each is an aliphatic, araliphatic or aromatic radical or is hydrogen, by reacting an N,N'-diformylalkylenediamine over a metal oxide catalyst, the improvement which comprises reacting an N,N'-diformyl-1,2-diamine of the formula

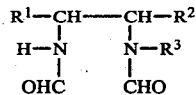

where $R^1$, $R^2$ and $R^3$ have the above meanings, in the gas phase, at from 200° to 350° C., in the presence of from 5 to 40 moles of an inert gas per mole of starting material II, over zinc oxide having a pore volume of from 0.05 to 1 milliliter per gram and a specific surface area of from 1 to 500 square meters per gram, or over a mixture of this zinc oxide and aluminum oxide, as the catalyst.

2. A process as claimed in claim 1, wherein the reaction is carried out at from 250° to 350° C.

3. A process as claimed in claim 1, wherein the reaction is carried out at from 260° to 340° C.

4. A process as claimed in claim 1, wherein the reaction is carried out under a pressure of not less than 1 bar.

5. A process as claimed in claim 1, wherein the reaction is carried out using a ratio of from 1 to 50 gram atoms of zinc per gram atom of aluminum.

6. A process as claimed in claim 1, wherein the reaction is carried out using from 0.1 to 1 gram atom of zinc per mole of starting material II.

7. A process as claimed in claim 1, wherein the reaction is carried out using a supported catalyst containing from 1 to 18 percent by weight, based on carrier, of the catalyst.

8. A process as claimed in claim 1, wherein the reaction is carried out using a catalyst of particle size from 0.05 to 7 millimeters.

9. A process as claimed in claim 1, wherein the reaction is carried out with a catalyst having a pore volume of from 0.1 to 0.8 millimeter per gram.

10. A process as claimed in claim 1, wherein the reaction is carried out with a catalyst having a specific surface area of from 30 to 150 square meters per gram.

11. A process as claimed in claim 1, wherein the reaction is carried out with a catalyst having a bulk density of from 0.4 to 2.1 grams per milliliter.

12. A process as claimed in claim 1, wherein the reaction is carried out with a catalyst having a pore radius of from 1.5 to 10 nanometers.

13. A process as claimed in claim 1, wherein the reaction is carried out in a fluidized bed of a catalyst in chip or bead form.

14. A process as claimed in claim 1, wherein the reaction is carried out using from 7 to 38 moles of inert gas per mole of starting material II.

15. A process as claimed in claims 1, 7, 8, 9 or 10 wherein the reaction is carried out with a catalyst having a bulk density of from 0.4 to 2.1 grams per milliliter and a pore radius of from 1.5 to 10 nanometers.

* * * * *

UNITED STATES PATENT AND TRADEMARK OFFICE
CERTIFICATE OF CORRECTION

PATENT NO. : 4,340,745
DATED : July 20, 1982
INVENTOR(S) : Toni Dockner, Uwe Kempe, Herbert Krug, Peter Magnussen and Werner Praetorius It is certified that error appears in the above-identified patent and that said Letters Patent are hereby corrected as shown below:

In Example 1 (col. 6, line 2): change the numeral "921"

to --0.921--; and

In Example 5 (col. 6, line 50): change the numeral "74"

to --7.4--.

Signed and Sealed this

Eighteenth Day of January 198.

[SEAL]

Attest:

GERALD J. MOSSINGHOFF

Attesting Officer   Commissioner of Patents and Trademarks